(12) United States Patent
Thiberg

(10) Patent No.: US 6,537,302 B1
(45) Date of Patent: Mar. 25, 2003

(54) MEANS FOR EXTERNAL MEDICAL TREATMENT BY MEANS OF LIGHT

(75) Inventor: Rolf Thiberg, Åkersberga (SE)

(73) Assignee: Biolight Patent Holding AB, Danderyd (SE)

( * ) Notice: Subject to any disclaimer, the term of this patent is extended or adjusted under 35 U.S.C. 154(b) by 0 days.

(21) Appl. No.: 09/889,211
(22) PCT Filed: Jan. 19, 2000
(86) PCT No.: PCT/SE00/00107
§ 371 (c)(1),
(2), (4) Date: Oct. 17, 2001
(87) PCT Pub. No.: WO00/43068
PCT Pub. Date: Jul. 27, 2000

(30) Foreign Application Priority Data

Jan. 20, 1999 (SE) .............................................. 9900160

(51) Int. Cl.[7] .................................................. A61N 5/01
(52) U.S. Cl. ................................ 607/88; 606/9; 606/13
(58) Field of Search ........................ 607/88, 89; 606/9, 606/13

(56) References Cited

U.S. PATENT DOCUMENTS 4,930,504 A * 6/1990 Diamantopoulos et al. ... 607/88
5,024,236 A * 6/1991 Shapiro ........................ 607/92
5,259,380 A * 11/1993 Mendes et al. ............. 607/115
5,358,503 A * 10/1994 Bertwell et al. ............... 607/88
5,500,009 A * 3/1996 Mendes et al. ................ 607/88
5,800,479 A * 9/1998 Thiberg ........................ 607/88
6,063,108 A * 5/2000 Salansky et al. .............. 607/89
6,238,424 B1 * 5/2001 Thiberg ........................ 607/88
6,238,425 B1 * 5/2001 Thiberg ........................ 607/88

FOREIGN PATENT DOCUMENTS

AT    305489    9/1971
FR    2731357   9/1996
SE    502784    7/1995

* cited by examiner

Primary Examiner—Roy D. Gibson
Assistant Examiner—Henry M. Johnson, III
(74) Attorney, Agent, or Firm—Alfred J. Mangels

(57) ABSTRACT

Apparatus for external medical treatment with the aid of light, including a light-emitting device to be held against or in close proximity to a patient's body. The device includes light-emitting diodes that emit monochromatic light over one or more predetermined time periods and that pulsate the emitted light in accordance with a predetermined pulse frequency or a series of pulse frequencies over the predetermined time periods. The light-emitting device includes a casing and a plate that carries the light-emitting diodes. An electric motor is fixedly mounted in the casing and is connected to the plate via a drive shaft, so that the plate with the light-emitting diodes performs a rotary movement.

7 Claims, 2 Drawing Sheets

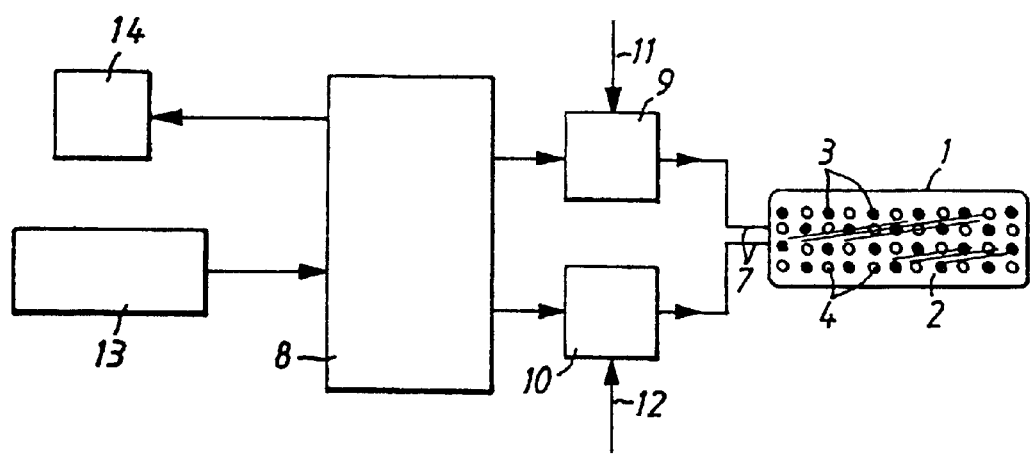
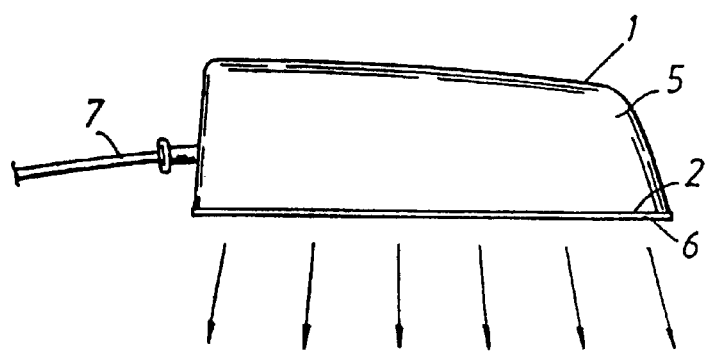

MEANS FOR EXTERNAL MEDICAL TREATMENT BY MEANS OF LIGHT

BACKGROUND OF THE INVENTION

1. Field of the Invention

The present invention relates to an apparatus for external medical treatment with the aid of light, more specifically with the aid of light which palliates and/or cures different states of diseases.

2. Description of the Related Art

Swedish Patent Specification No. 502 784 teaches an apparatus for external medical treatment with the aid of light that includes a light-emitting device which is intended to be held against or close to the body of an individual, and drive means for the light-emitting device. The light-emitting device includes light-emitting diodes or corresponding elements which are intended to emit infrared light. According to the aforesaid patent specification, the means for driving the light-emitting device is adapted to control said device to emit infrared-light in a first stage over a first predetermined time period and then to emit visible light in a second stage over a second predetermined time period, wherein said drive means is adapted to pulsate the infrared light and the visible light in accordance with a predetermined series of pulse frequencies.

It is also known to emit other types of monochromatic light for treating different states of diseases.

It has also been found that very good results can be obtained when treating a patient with solely one or more types of monochromatic light and with light other than infrared light, such as visible light of different colors emitted in accordance with a given pulse frequency.

It has been found that an apparatus of the aforesaid kind can be used very successfully for treating many different states of diseases and injuries, for instance sports injuries, stretched muscles, muscular pain, joint pain, headaches, various inflammatory conditions, various skin complaints, such as acne, back pains, etc., provided that the light is emitted in a certain way. In this regard, treatment with light has a favorable influence on injury-healing processes and will palliate and/or cure various diseases.

There is thus an understanding that treatment with certain light that is emitted in certain frequency series will have a significantly greater effect in shortening the time taken to cure or palliate a disease.

One problem with devices of this kind known hitherto is that the person administering the treatment is required to oscillate the light-emitting device while holding the device against or in close proximity to that region of the patient's body to be treated. The reason for this is because the light-emitting diodes disposed at the bottom of the light-emitting device have a given geometric extension and are of different kinds, and hence two mutually adjacent light-emitting diodes of mutually the same kind will be spaced at a certain distance apart. It is therefore necessary to move the light-emitting device forwards and backwards over the area to be treated, in order to ensure that the whole of said area will be irradiated uniformly to the best possible extent.

Because treatment of this kind will usually take from two to ten minutes to carry out, frequent administration of the treatment administered may be very onerous to the person concerned.

This problem is solved by the present invention.

SUMMARY OF THE INVENTION

Thus, the present invention relates to an apparatus which is intended for external medical treatment with the aid of light. The apparatus includes a light-emitting device that is intended to lie against or to be held in close proximity to the patient's body, wherein the light-emitting device includes light-emitting diodes or corresponding elements which are adapted to emit monochromatic light. Drive means that drives said device is adapted to control the light-emitting device to emit one or more types of monochromatic light over one or more predetermined time periods, and to pulsate said emitted light in accordance with a predetermined pulse frequency or series of pulse frequencies over said time periods. The light-emitting device includes a casing and a light-emitting-diode supporting plate, and includes an electric motor which is fixed in relation to said casing and connected to said plate via a drive shaft, so that the plate carrying the light-emitting diodes performs a rotary movement.

BRIEF DESCRIPTION OF THE DRAWINGS

The invention will now be described in more detail partly with reference to an exemplifying embodiment thereof shown on the accompanying drawings, in which FIG. 1 is a schematic block diagram illustrating an apparatus of the aforesaid kind;

FIG. 2 is a side view of a light-emitting device;

DESCRIPTION OF THE PREFERRED EMBODIMENTS

Figure 3:
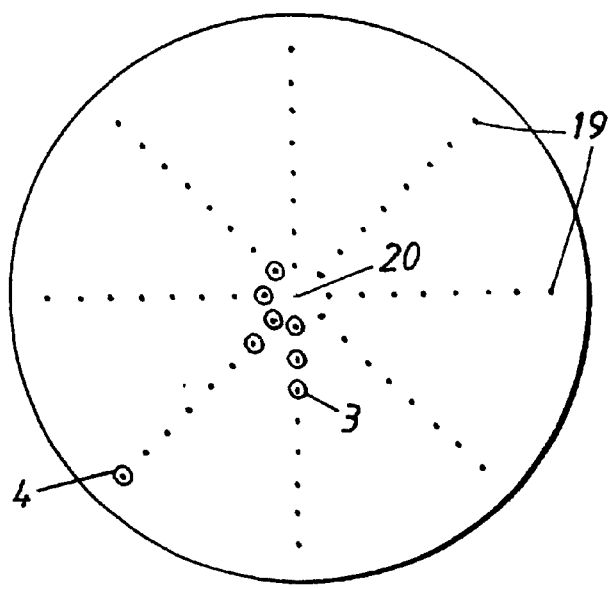
FIG. 3 shows an inventive light-emitting device from beneath.

FIGS. 1 and 2 illustrate generally an apparatus for external medical treatment with the aid of light, said apparatus including a light-emitting device 1 which is intended to be held against or in close proximity to the patient's body. The light-emitting device 1 is shown from one side in FIG. 2 and from beneath in FIG. 1. This device 1 includes a casing 5 which houses a transparent plate 6. Located beneath the plate 6 is a surface 2 on which a plurality of light-emitting diodes 3, 4 or corresponding elements are mounted.

The light-emitting diodes thus emit light through the plate 6 when energized, i.e. when supplied with current through a cable 7.

When the device is being used, the casing 5 is held so that the plate 6 will lie against the relevant part of the patient's body.

The apparatus also includes drive means for the light-emitting device 1. The drive means is adapted to control the light-emitting device 1 to emit different monochromatic light of different wavelengths over different predetermined time periods, and to pulsate the light emitted in accordance with a predetermined pulse frequency or series of pulse frequencies over said time periods.

The light-emitting device 1 may include light-emitting diodes 3 adapted for the emission of infrared light. These diodes are shown with solid circles in FIG. 1. Visible light can be emitted with the aid of other light-emitting diodes 4. These diodes are illustrated with empty circles in FIG. 1. The infrared light diodes 3 will preferably be semiconductors of the GaAs-type (Gallium Arsenide). The diodes 4 that emit visible light will also preferably be of the GaAs-type.

The drive means includes a computer 8 which controls drive circuits 9, 10 to which signals for driving the light-emitting diodes are sent from the computer via conductor 7.

The computer and the drive circuits are of a suitable known kind. The drive means or computer has connected thereto a keyboard 13 by means of which the operator can key-in data for causing the drive means to activate the light-emitting device in a desired manner. The device will conveniently also include a display 14 for displaying the settings entered through the keyboard. This display may be the computer screen.

The light-emitting device 1 includes light-emitting diodes 4 which are adapted to emit essentially monochromatic visible light in one of the colors violet, blue, yellow, orange, red or green, and also infrared light and other invisible wavelengths.

The nature of the light used will depend on the disease or the type of injury to be treated.

A large part of the above description of the drawings is also found in the aforementioned patent specification.

Figure 4:
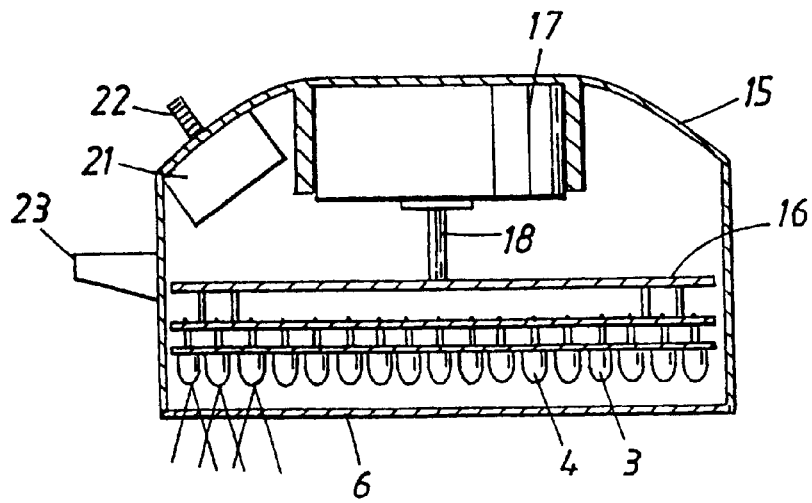
FIG. 4 is a cross-sectional view of the inventive light-emitting device.

According to the present invention, as shown in FIGS. 3 and 4, the light-emitting device 1 includes a casing 15 and a plate 16 that carries the light-emitting diodes 3, 4.

In accordance with the present invention the apparatus includes an electric motor 17 that is fixedly mounted relative to the casing 15 and which is connected to said plate 16 via a drive shaft 18, whereby the plate 16 carrying the light-emitting diodes 3, 4 will perform a rotary movement relative to the casing 15 when the motor is running.

The various light-emitting diodes will therefore be moved forwards over the area of the body to be treated and will provide totally uniform irradiation of said area without the person administering the treatment needing to move the apparatus forwards and backwards over said area.

According to one preferred embodiment of the invention, the light-emitting diodes are mounted on said plate 16 around concentric circles relative to the drive shaft 18, as illustrated in FIG. 3, where each dot 19 denotes the location of a light-emitting diode. The diodes disposed around a circle on the plate may either be of one and the same kind, or diodes of one and the same kind may be placed radially outwards from the center 20 of the plate.

According to one alternative embodiment, the light-emitting diodes are mounted on the plate 16 around a helical line in relation to the drive shaft 18, i.e. from the center of the plate and radially out towards the plate periphery.

According to one preferred embodiment, the plate 16 is rotated at a speed of about 1 to 200 r.p.m. The motor 17 is preferably a stepping motor. The motor may also be constructed for rotation in both directions.

According to another preferred embodiment, the electric motor 17 is a variable speed motor. To this end, an appropriate known control circuit 21 may be fitted in the casing 15. An outwardly projecting knob 22 may be provided for finger adjustment of the motor speed.

In FIG. 4, the reference 23 identifies an input for an electric cable for driving the motor and the light-emitting diodes. The control circuit 21 may be included in said drive means 8, 9, 10. In this case, the motor may be activated via the cable, therewith obviating the need for a separate control circuit 21 in the light-emitting device 1. The motor speed may be keyed-in on the key pad 13.

It will be obvious that the present invention solves the problem mentioned in the introduction.

The invention has been described above with reference to certain embodiments thereof.

It will, however, be understood that the present invention is not restricted to these embodiments but that variations can be made within the scope of the accompanying claims.

What is claimed is:

1. Apparatus for external medical treatment with the aid of light, said apparatus comprising: a light-emitting device to be held in close proximity to a patient's body, wherein said light-emitting device includes light-emitting elements that emit monochromatic light, drive means for controlling the light-emitting device to emit at least one type of monochromatic light over at least one predetermined time period and to pulsate said emitted light in accordance with a predetermined pulse frequency over said at least one time period, and wherein said light-emitting device includes a casing and a plate that carries said light-emitting elements, an electric motor fixedly mounted in relation to said casing and connected to said plate via a drive shaft, whereby the plate with the light-emitting elements rotates when the motor is energized to rotate the drive shaft.

2. Apparatus according to claim 1, wherein the light-emitting elements are mounted on said plate in circles that are concentric with the drive shaft.

3. Apparatus according to claim 1, wherein the light-emitting elements are mounted on said plate along a helical line relative to the drive shaft.

4. Apparatus according to claim 1, wherein the electric motor is driven at a speed of about 1 to 200 r.p.m.

5. Apparatus according to claim 1, wherein the electric motor is a variable speed motor.

6. Apparatus according to claim 1, wherein the electric motor is a stepping motor.

7. Apparatus according to claim 1, wherein the light-emitting elements are light-emitting diodes.

\* \* \* \* \*